(12) United States Patent
Camilleri et al.

(10) Patent No.: US 7,005,300 B1
(45) Date of Patent: Feb. 28, 2006

(54) POLYHYDROXY DIAMINE SURFACTANTS AND THEIR USE IN GENE TRANSFER

(75) Inventors: Patrick Camilleri, Harlow (GB); Jan Bernard Frederik Nicolaas Engberts, Groningen (NL); Matthew Leigh Fielden, Örsundsbro (SE); Andreas Kremer, Leverkusen (DE)

(73) Assignee: SmithKlineBeecham plc, Brentford (GB)

( * ) Notice: Subject to any disclaimer, the term of this patent is extended or adjusted under 35 U.S.C. 154(b) by 419 days.

(21) Appl. No.: 10/018,712

(22) PCT Filed: Jun. 16, 2000

(86) PCT No.: PCT/GB00/02365

§ 371 (c)(1),
(2), (4) Date: Aug. 5, 2002

(87) PCT Pub. No.: WO00/76954

PCT Pub. Date: Dec. 21, 2000

(30) Foreign Application Priority Data

Jun. 16, 1999 (GB) .................................... 9914085

(51) Int. Cl.
*C12H 15/88* (2006.01)

(52) U.S. Cl. ...................... 435/458; 536/18.7; 514/44; 424/450

(58) Field of Classification Search ................. 435/458
See application file for complete search history.

(56) References Cited

PUBLICATIONS

Gleave, M. et al., "Clusterin and IGFBPs as Antisense Targets in Prostate Cancer", 2003, Ann. N.Y. Acad. Sci.Vol. 1002: pp. 95-104.*
Juengst, E.T., "What next for human gene therapy?", 2003, BMJ, vol. 326: pp. 1410-1411.*
Berzofsky, J.A., et al., "Progress on new vacine strategies for the immunotherapy and prevention of cancer", 2004, J. Clin. Invest., vol. 113: pp. 1515-1525.*

Dang, C.V., et al., "Gene Therapy and Translational Cancer Research", 1999, Clin. Cancer Res., vol. 5: pp. 471-474.*
Restifo, N.P. et al., "The promise of nucleic acid vaccines". 2000, Gene Therapy, vol. 7:, pp. 89-92.*
Madigan, M.T. et al., in "Biology of Macroorganisms", 1997, Eighth Edition, Prentice Hall, pp. 323-324.*
Sambrook et al., in "Molecular Cloning: A Laboratory Manual", 1995, Cold Spring Harbor Laboratory Press, pp. 1.74-1.75.*
Gao, et al., "Cationic Liposome-Mediated Gene Transfer". *Gene Therapy*, GB, MacMillan Press Ltd., Basingstoke, 2(*10*): 710-722 (Dec. 1, 1995).
Pestman, et al., "Nonionic Bolaamphiphiles and Gemini Surfactants Based on Carbohydrates", *Langmuir*, *13*: 6857-6860 (1997).

* cited by examiner

*Primary Examiner*—Scott D. Priebe
*Assistant Examiner*—Michael Burkhart
(74) *Attorney, Agent, or Firm*—Reid S. Willis; William R. Majarian; Charles M. Kinzig

(57) ABSTRACT

The use of carbohydrate-based surfactant compounds having the general formula (I):

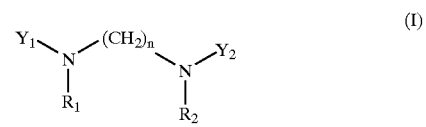

wherein $Y_1$ and $Y_2$, which may be the same or different, are carbohydrate groups;
$R_1$ and $R_2$, which may be the same or different, are selected from:
  a) hydrogen;
  b) $C_{(1-24)}$ alkyl group;
  c) $C_{(1-24)}$ alkyl carboxy group; or
  d) a carbon chain of 2 to 24 carbon atoms having one or more carbon/carbon double bonds,
  and n is from 1 to 10;
  for facilitating the transfer of DNA or RNA polynucleotides, or analogs thereof, into a eukaryotic or prokaryotic cell in vivo or in vitro.

New carbohydrate-based surfactant compounds are also disclosed.

16 Claims, 3 Drawing Sheets

POLYHYDROXY DIAMINE SURFACTANTS AND THEIR USE IN GENE TRANSFER

NEW USE

This invention relates to new uses for carbohydrate-based surfactant compounds. Such uses include facilitating the transfer of compounds into cells for drug delivery and facilitating the transfer of oligonucleotides and polynucleotides into cells for gene expression studies or gene therapy. The invention also relates to new carbohydrate-based surfactant compounds and methods for their production.

Surfactants are substances that markedly affect the surface properties of a liquid, even at low concentrations. For example surfactants will significantly reduce surface tension when dissolved in water or aqueous solutions and will reduce interfacial tension between two liquids or a liquid and a solid. This property of surfactant molecules has been widely exploited in industry, particularly in the detergent and oil industries. In the 1970s a new class of surfactant molecule was reported, characterised by two hydrophobic chains with polar heads which are linked by a hydrophobic bridge (Deinega, Y et al., *Kolloidn. Zh.* 36, 649, 1974). These molecules, which have been termed "gemini" (Menger, F M and Littau, C A, *J. Am. Chem. Soc.* 113, 1451, 1991), have very desirable properties over their monomeric equivalents. For example they are highly effective in reducing interfacial tension between oil and water based liquids and have a very low critical micelle concentration. Recently, Pestman et al have reported the synthesis and characterisation of nonionic carbohydrate-based gemini surfactants (Pestman, J M et al, Langmuir, 13, 6857–6860, 1997).

Cationic surfactants have been used inter alia for the transfection of polynucleotides into cells in culture, and there are examples of such agents available commercially to scientists involved in genetic technologies (for example the reagent Tfx™-50 for the transfection of eukaryotic cells available from Promega Corp. WI, USA).

The efficient delivery of DNA to cells in vivo, either for gene therapy or for antisense therapy, has been a major goal for some years. Much attention has concentrated on the use of viruses as delivery vehicles, for example adenoviruses for epithelial cells in the respiratory tract with a view to corrective gene therapy for cystic fibrosis (CF). However, despite some evidence of successful gene transfer in CF patients, the adenovirus route remains problematic due to inflammatory side-effects and limited transient expression of the transferred gene. Several alternative methods for in vivo gene delivery have been investigated, including studies using cationic surfactants. Gao, X et al. (1995) *Gene Ther.* 2, 710–722 demonstrated the feasibility of this approach with a normal human gene for CF transmembrane conductance regulator (CFTR) into the respiratory epithelium of CF mice using amine carrying cationic lipids. This group followed up with a liposomal CF gene therapy trial which, although only partially successful, demonstrated the potential for this approach in humans (Caplen, N J. et al., *Nature Medicine,* 1, 39–46, 1995). More recently other groups have investigated the potential of other cationic lipids for gene delivery, for example cholesterol derivatives (Oudrhiri, N et al. *Proc. Natl. Acad. Sci.* 94, 1651–1656, 1997). This limited study demonstrated the ability of these cholesterol based compounds to facilitate the transfer of genes into epithelial cells both in vitro and in vivo, thereby lending support to the validity of this general approach.

These studies, and others, show that in this new field of research there is a continuing need to develop novel low-toxicity surfactant molecules to facilitate the effective transfer of polynucleotides into cells both in vitro for transfection in cell-based experimentation and in vivo for gene therapy and antisense treatments. The present invention seeks to overcome the difficulties exhibited by existing compounds.

The invention relates to the use of carbohydrate-based surfactant compounds having the general formula (1):

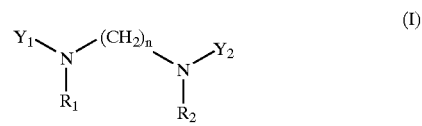

wherein $Y_1$ and $Y_2$, which may be the same or different, are carbohydrate groups, preferably sugars;

$R_1$ and $R_2$, which may be the same or different, are selected from:
  a) hydrogen;
  b) $C_{(1-24)}$ alkyl group;
  c) $C_{(1-24)}$ alkyl carboxy group; or
  d) a carbon chain of 2 to 24 carbon atoms having one or more carbon/carbon double bonds, and n is from 1 to 10;

or a salt, preferably a pharmaceutically acceptable salt thereof, for facilitating the transfer of DNA or RNA polynucleotides, or analogs thereof, into a eukaryotic or prokaryotic cell in vivo or in vitro.

Preferably the compound is symmetrical, that is the groups $R_1$ and $R_2$ are the same, and $Y_1$ and $Y_2$ are the same. The molecular symmetry allows these compounds to be referred to as "gemini" surfactants.

In a preferred embodiment, the carbohydrate groups $Y_1$ and $Y_2$ are sugars, attached to the nitrogen via a reduced imine bond. Such sugars include monosaccharides such as glucose and fructose, disaccharides such as lactose and more complex sugars, for instance sugars based on cellulose.

In a particularly preferred embodiment, $Y_1$ and $Y_2$ are glucose; the compounds having the general structure of formula (II):

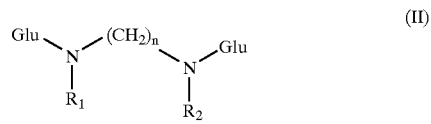

wherein Glu is glucose in open chain form (glucitol) linked via the C-1 (aldehyde carbon), and $R_1$, $R_2$ and n are as hereinbefore defined.

In a further preferred embodiment $R_1$ and $R_2$ are alkyl groups of chain-length $C_{(10-20)}$, most preferably $C_{(12-18)}$, and n is between 2 and 8, most preferably 4 or 6.

In a still further preferred embodiment $R_1$ and $R_2$ are $C_{(12-24)}$, preferably $C_{(16-20)}$, most preferably $C_{18}$ carbon chains having one or more carbon/carbon double bonds.

Such compounds are new and form part of the present invention.

The present invention shows the surprising finding that carbohydrate-based surfactants are highly efficient agents for facilitating the transfection of polynucleotides into cells.

Compounds of formula (1) in which $R_1$ and $R_2$ are not both $C_{(1-24)}$ alkyl carboxyl groups are new. Accordingly, in a further aspect, the present invention provides for compounds of formula (I) in which one of $R_1$ or $R_2$ is an alkyl group of chain-length $C_{(1-24)}$, and the other is a $C_{(1-24)}$ alkyl carboxy group.

Compounds of the present invention may be prepared from readily available starting materials using synthetic chemistry well known to the skilled person. A general process for preparing carbohydrate-based surfactant compounds comprises the addition of carbohydrate groups at the amine ends of an alkyl diamine compound. The following is a general scheme (scheme 1) for the synthesis of the sugar-based compounds of the invention, as illustrated for glucose-based compounds:

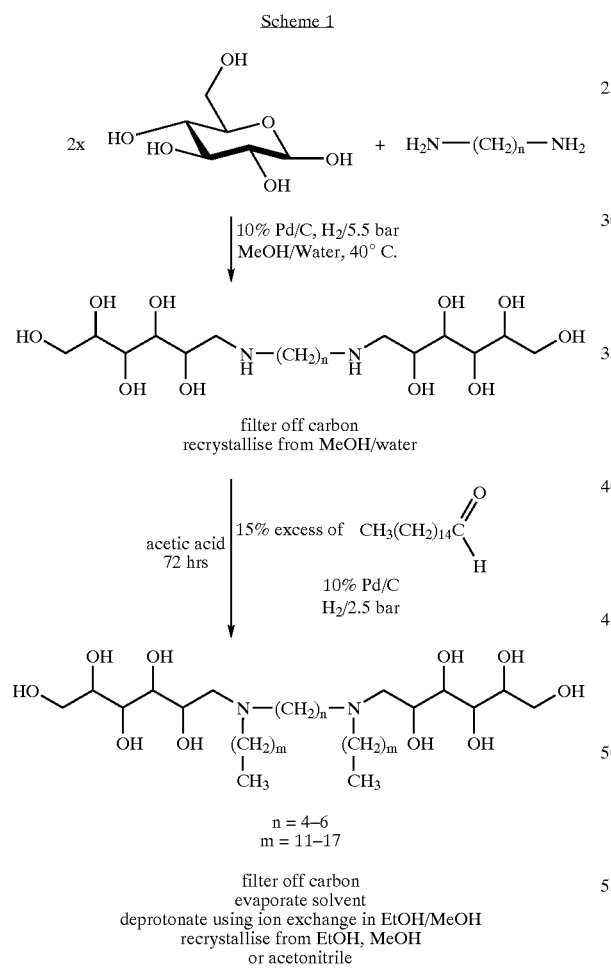

For $R_1=C_{(1-24)}$ alkyl carboxy, the second step will be the formation of an amide bond, using a suitable acylating agent, for instance an activated derivative of the corresponding acid.

Preferably the scheme for the synthesis of the sugar-based compounds of the invention, as illustrated for glucose-based compounds, is as shown in scheme 2:

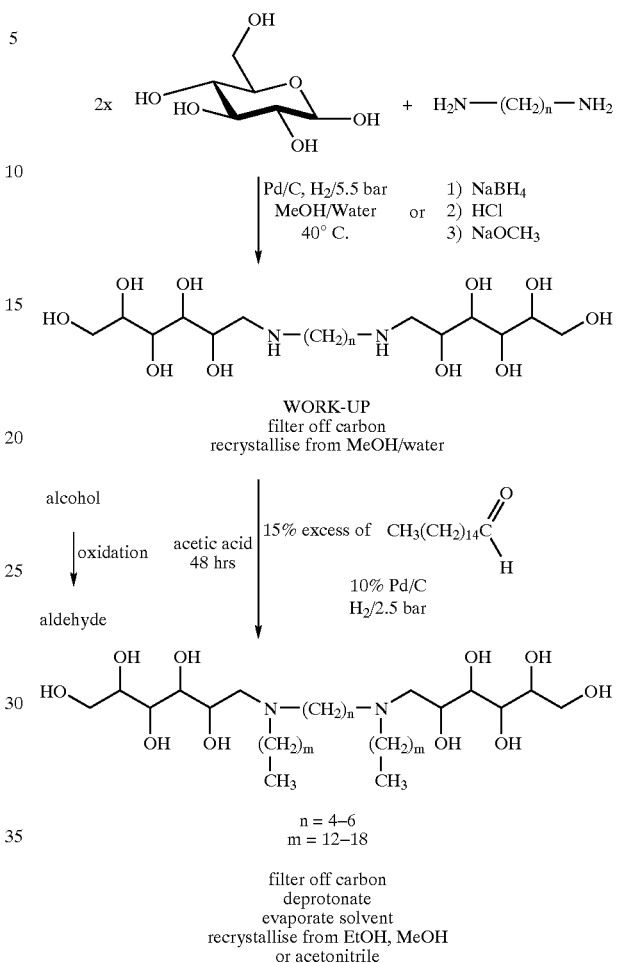

In a further aspect, the compounds of the invention which comprise carbon chains of 2 to 24 carbon atoms and having one or more carbon/carbon double bonds may be prepared according to scheme 3 (FIG. 3) as exemplified for the $C_{18}$ oleyl compound. The skilled person can use this information to devise analogous processes for preparing other compounds comprising carbon chains of 2 to 24 carbon atoms and having one or more carbon/carbon double bonds.

The processeses described above are for the synthesis of symmetrical, that is "gemini", carbohydrate-based surfactants. Non-symmetrical carbohydrate-based surfactants of the invention can be prepared by introducing asymmetry, for example at the primary amines of the diamine, by using different protecting groups.

In a further aspect, the carbohydrate-based surfactant compounds are used to facilitate the transfer of oligonucleotides and polynucleotides into cells to achieve an antisense knock-out effect, for gene therapy and genetic immunisation (for the generation of antibodies) in whole organisms. In a further preferred embodiment, the carbohydrate-based surfactant compounds are used to facilitate the transfection of polynucleotides into cells in culture when such transfer is required, in, for example, gene expression studies and antisense control experiments among others. The polynucleotides can be mixed with the compounds, added to the cells and incubated to allow polynucleotide uptake. After further incubation the cells can be assayed for the phenotypic trait afforded by the transfected DNA, or the levels of mRNA expressed from said DNA can be determined by Northern blotting or by using PCR-based quantitation methods for example the Taqman™ method (Perkin Elmer, Connecticut, USA). Compounds of the invention offer a significant improvement, typically between 3 and 6 fold, in the efficiency of cellular uptake of DNA in cells in culture, compared with compounds in the previous art. In the transfection protocol, the gemini compound may be used in combination with one or more supplements to increase the efficiency of transfection. Such supplements may be selected from, for example:

(i) a neutral carrier, for example dioleyl phosphatidylethanolamine (DOPE) (Farhood, H., et al (1985) *Biochim. Biophys. Acta* 1235 289);

(ii) a complexing reagent, for example the commercially available PLUS reagent (Life Technologies Inc. Maryland, USA) or peptides, such as polylysine or polyornithine peptides or peptides comprising primarily, but not exclusively, basic amino acids such as lysine, ornithine and/or arginine. The list above is not intended to be exhaustive and other supplements that increase the efficiency of transfection are taken to fall within the scope of the invention.

In still another aspect, the invention relates to the transfer of genetic material in gene therapy using the compounds of the invention.

Yet another aspect of the invention relates to methods to effect the delivery of non-nucleotide based drug compounds into cells in vitro and in vivo using the compounds of the invention.

In a further aspect, the invention relates to methods to facilitate the transfer of a polynucleotide or an anti-infective compounds into prokaryotic or eukaryotic organism for use in anti-infective therapy.

The following definitions are provided to facilitate understanding of certain terms used frequently herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Transfection" refers to the introduction of polynucleotides into cells in culture using methods involving the modification of the cell membrane either by chemical or physical means. Such methods are described in, for example, Sambrook et al., *MOLECULAR CLONING: A LABORATORY MANUAL*, 2nd Ed., Cold Spring Harbor Laboratory Press, Cold Spring Harbor, N.Y. (1989). The polynucleotides may be linear or circular, single-stranded or double-stranded and may include elements controlling replication of the polynucleotide or expression of homologous or heterologous genes which may comprise part of the polynucleotide.

The invention will now be described by way of the following examples.

EXAMPLE 1

Transfection of Recombinant Plasmid Expressing Luciferase into Cells in Culture Using Carbohydrate-Based Surfactant Compounds Carbohydrate-based surfactant compounds having the general structure of formula (II)

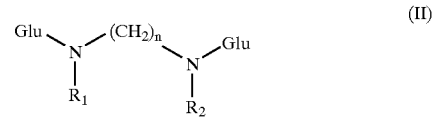

(II)

were synthesised according to the method as hereinbefore described. The following compounds were made:

| Compound no. | $R_1$-n-$R_2$ |
|---|---|
| GS_G_1: | 16-6-16 |
| GS_G_2: | 18-6-18 (unsaturated (oleyl) R chains) |
| GS_G_3: | 12-6-12 |
| GS_G_4: | 14-6-14 |
| GS_G_5: | 14-4-14 |
| GS_G_6: | 16-4-16 |
| GS_G_7: | 12-4-12 |
| GS_G_8: | 18-4-18 |
| GS_G_9: | 18-6-18 |

Transfection studies were performed using the adherent cell line CHO-K1 (Puck et al. 1958). Complete medium consisted of MEM alpha medium supplemented with 10% v/v foetal bovine serum and 1× L-Glutamine. All media and supplements were obtained from Life Technologies.

Stable transfected cell lines expressing β-galactosidase were generated by cotransfection of the plasmid pSV-β-Galactosidase Control Vector (Promega) with the plasmid Selecta Vecta-Neo (R & D Systems) in a 10:1 ratio. Following G418 (Life Technologies) selection (0.8 mg ml$^{-1}$), candidate cell lines were tested for β-galactosidase activity (β-Gal Reporter Gene Assay, chemiluminescent; Roche Diagnostics).

In Vitro Gene Transfection.

Cells were seeded into 96-well plates (Beckton Dickinson) 16–18 hours prior to transfection at an approximate density of 1×10$^4$ cells per well. For transfection, 64 ng of the luciferase reporter gene plasmid, pGL3-Control Vector (Promega) per well, was incubated with various concentrations of the carbohydrate-based gemini compounds. After 30 minutes incubation at RT, OPTI-MEM™ medium (Life Technologies) was added to the transfection mixture and the solution placed on the cells (final volume per well: 100 μl). Following a 3 hour or over night incubation at 37° C., the transfection solution was replaced with complete medium and the cells incubated further at 37° C. Reporter gene assays were performed according to the manufacturer's guidelines (Roche Diagnostics) approximately 48 hours post transfection. Luminescence was measured in a Packard TopCount NXT Microplate Scintillation and Luminescence Counter. For normalization purpose, β-galactosidase activity (β-Gal Reporter Gene Assay, chemiluminescent; Roche Diagnostics) was measured and luciferase activity per β-galactosidase activity was calculated. The results are shown in FIGS. 1 and 2.

EXAMPLE 2

Transfection Efficiency of GS_G_2 in the Presence or absence of foetal Calf Serum (FCS)

GS_G_2 was prepared as described hereinabove and used in experiments to test the transfection efficiency of the compound as described in example 1. Two experiments were conducted, in both experiments the compound was tested at 4 uM, 8 uM, 10 uM, 20 uM and 30 uM both in the presence and absence of PLUS reagent. In the first experiment the CHO-K1 cells were incubated overnight without foetal calf serum (FCS) and in the second experiment the CHO-K1 cells were incubated overnight in the presence of FCS. The results showed that preincubation with foetal calf serum had no effect on the transfection efficiency of the GS_G_2 compound. This result was surprising as it is well known in the art that serum reduces transfection efficiency. The presence or absence of PLUS reagent had no significant effect on transfection efficiency in either experiment.

Figure 1:
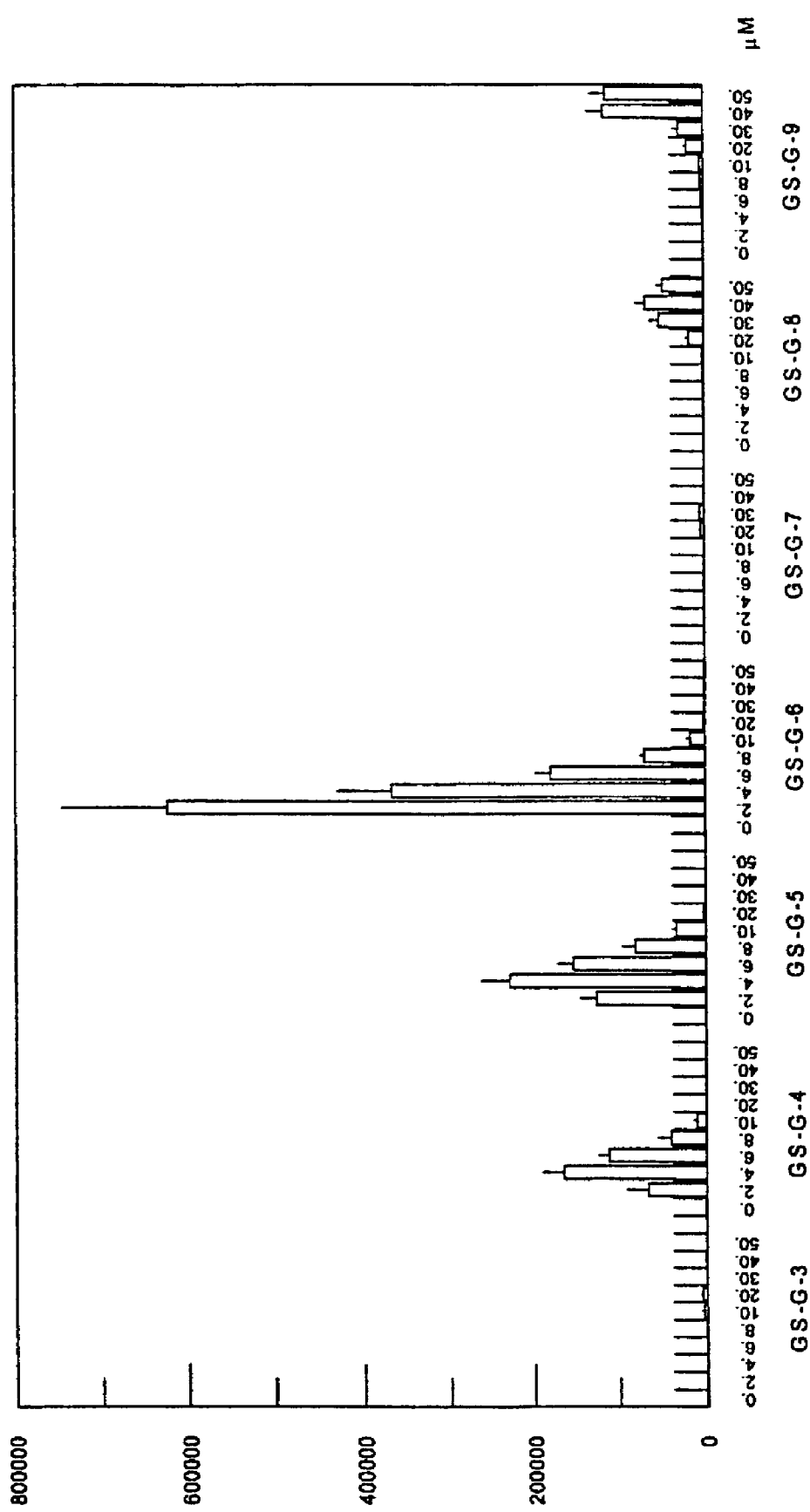
FIG. 1. Transfection of CHO-K1 cells (stable transfected with beta-galactosidase) with carbohydrate-based gemini compounds GS-G-3, GS-G4, GS-G-5, GS-G-6, GS-G-7, GS-G-8, and GS-G-9. Concentrations of the compounds in μM is shown on the x axis. Bars represent the mean cps (counts per second) of 8 experiments±the standard error of the mean.
Figure 2:
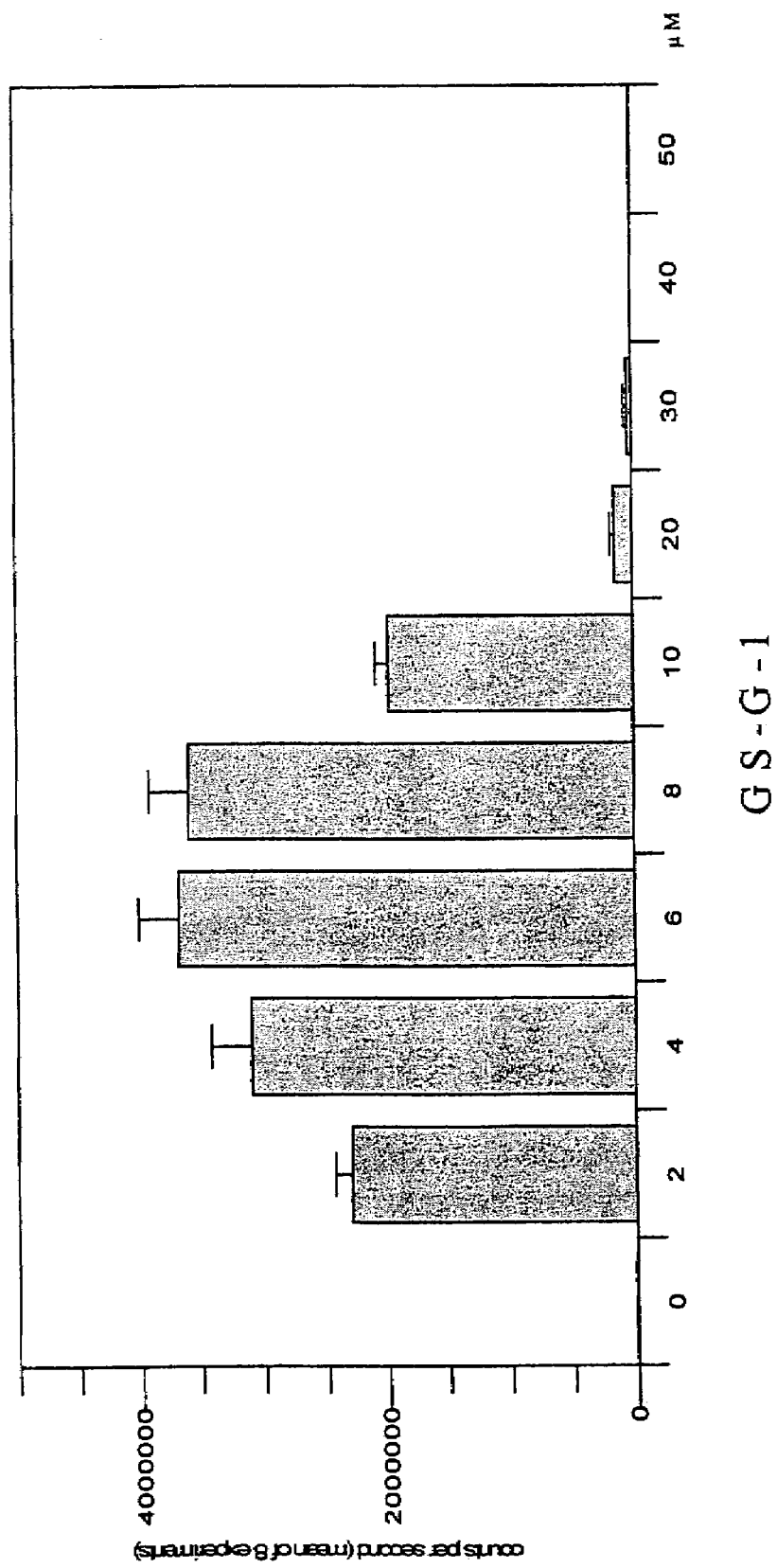
FIG. 2. Transfection of CHO-K1 cells (stable transfected with beta-galactosidase) with carbohydrate-based gemini compound GS-G-1. Concentrations of the compound in μM is shown on the x axis. Bars represent the mean cps (counts per second) of 8 experiments±the standard error of the mean.
Figure 3:
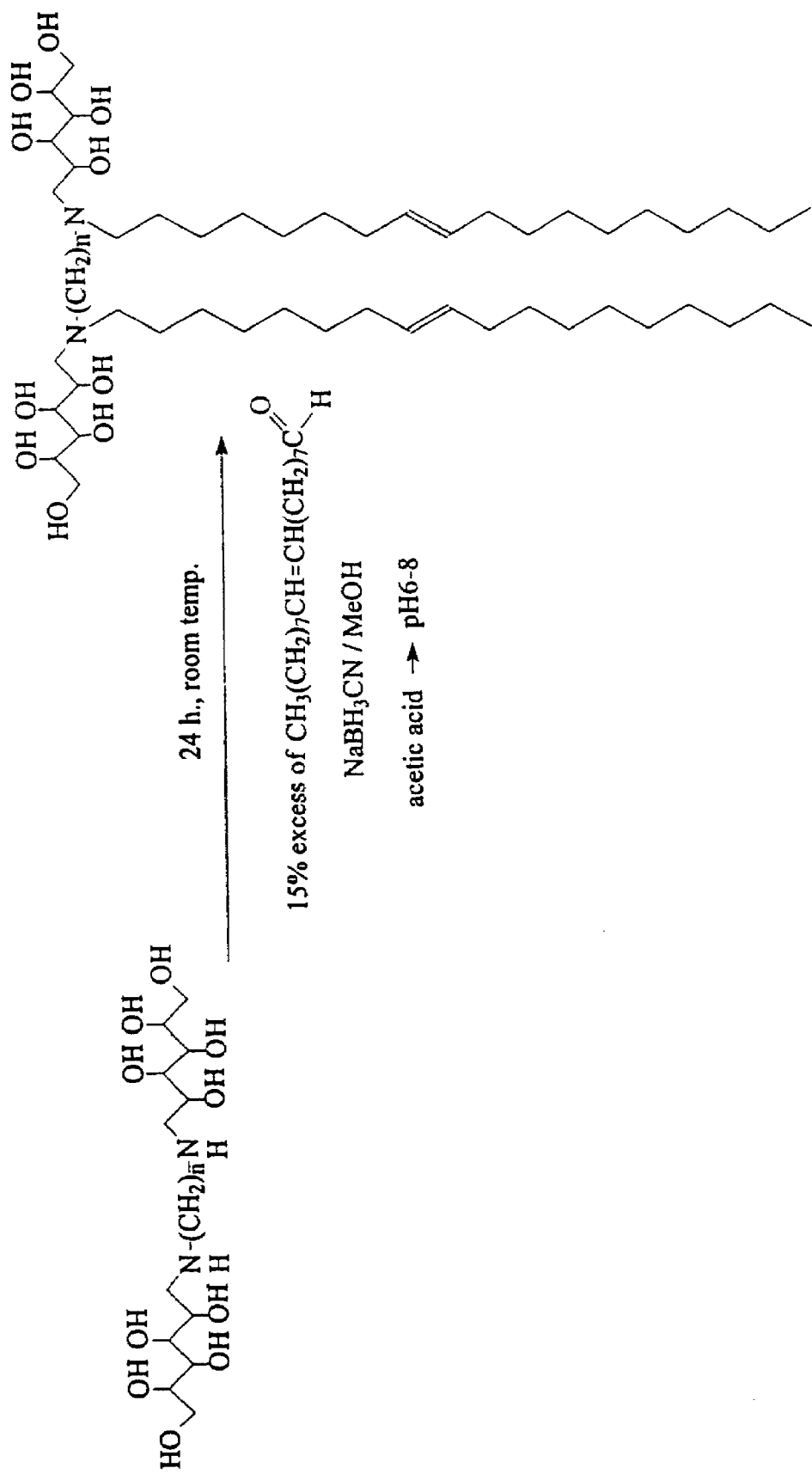
FIG. 3. Scheme 3 shows a general process for the preparation of an oleyl compound of the invention.

The invention claimed is:

1. A method of transferring a DNA or RNA polynucleotide into a eukaryotic cell in vivo or in vitro, the method comprising contacting the cell with a DNA or RNA polynucleotide and a compound of formula (I):

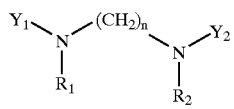

(I)

wherein $Y_1$ and $Y_2$, which may be the same or different, are carbohydrate groups;
$R_1$ and $R_2$, which may be the same or different, are selected from the group consisting of:
hydrogen,
$C_{(1-24)}$ alkyl group,
$C_{(1-24)}$ alkyl carboxy group, and
a carbon chain of 2 to 24 carbon atoms having one or more carbon/carbon double bonds;
and n is from 1 to 10;
or a pharmaceutically acceptable salt thereof.

2. The method of claim 1 wherein the carbohydrate groups $Y_1$ and $Y_2$ are sugars.

3. The method of claim 1 wherein $R_1$ and $R_2$ are alkyl groups of chain-length $C_{(10-20)}$ and n is between 2 and 8.

4. The method of claim 3 wherein $R_1$ and $R_2$ are alkyl groups of chain-length $C_{(12-18)}$ and n is 4 or 6.

5. The method of claim 1 wherein $R_1$ and $R_2$ are carbon chains of 2 to 24 carbon atoms having one or more carbon/carbon double bonds.

6. The method of claim 5 wherein the carbon chains have 18 carbon atoms.

7. The method of claim 1 wherein the compound is symmetrical, that is the groups $R_1$ and $R_2$ are the same, and $Y_1$ and $Y_2$ are the same.

8. The method of claim 1 wherein the polynucleotide is transferred into the cell in culture.

9. A compound of formula (I):

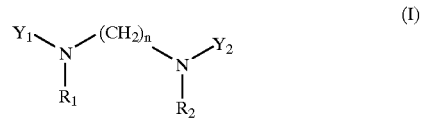

(I)

wherein Y1 and Y2, which may be the same or different, are carbohydrate groups; one of R1 and R2 is selected from the group consisting of hydrogen, a $C_{(1-24)}$ alkyl group, a $C_{(1-24)}$ alkylcarboxy group, and a carbon chain of 2 to 24 carbon atoms having one or more carbon/carbon double bonds; the other of R1 and R2 is selected from the group consisting of a $C_{(1-24)}$ alkyl group and a carbon chain of 2 to 24 carbon atoms having one or more carbon/carbon double bonds; and n is from 1 to 10; or a pharmaceutically acceptable salt thereof.

10. The compound of claim 9 wherein $R_1$ and $R_2$ are alkyl groups of chain-length $C_{(10-20)}$ and n is between 2 and 8.

11. The compound of claim 9 wherein $R_1$ and $R_2$ are each oleyl, $C_{12}$-alkyl, $C_{14}$-alkyl, $C_{16}$-alkyl, or $C_{18}$-alkyl; $Y_1$ and $Y_2$ are each glucitol; and n is 4 or 6.

12. The compound of claim 9 wherein the compound is a gemini compound where $R_1$ and $R_2$ are the same and $Y_1$ and $Y_2$ are the same.

13. The compound of claim 12 which has the formula (II):

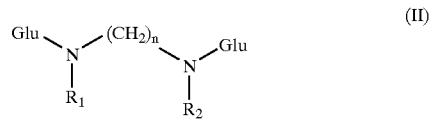

(II)

wherein Glu is glucose in open chain form (glucitol).

14. The compound of claim 9 wherein one of $R_1$ and $R_2$ is an alkyl group of chain-length $C_{(1-24)}$, and the other of $R_1$ and $R_2$ is a $C_{(1-24)}$ alkyl carboxy group.

15. The compound of claim 9 wherein $R_1$ and $R_2$ are carbon chains of 2 to 24 carbon atoms having one or more carbon/carbon double bonds.

16. The compound of claim 15 wherein the carbon chain has 18 carbon atoms.

* * * * *

UNITED STATES PATENT AND TRADEMARK OFFICE
CERTIFICATE OF CORRECTION

PATENT NO.    : 7,005,300 B1
DATED         : February 28, 2006
INVENTOR(S)   : Weber et al.

Page 1 of 1

It is certified that error appears in the above-identified patent and that said Letters Patent is hereby corrected as shown below:

<u>Column 57,</u>
Line 13, change "RO M" to -- ROM --.

Signed and Sealed this

Ninth Day of May, 2006

JON W. DUDAS
*Director of the United States Patent and Trademark Office*